United States Patent [19]
Anderson

[11] 3,938,517
[45] Feb. 17, 1976

[54] TEAT CAUTERY BULLET

[76] Inventor: Carsten D. Anderson, 1307 N. Summer Range Road, DePere, Wis. 54115

[22] Filed: Mar. 14, 1975

[21] Appl. No.: 558,314

[52] U.S. Cl. ............ 128/271; 128/341; 119/14.19; 128/267
[51] Int. Cl.² ................. A61M 35/00; A61M 31/00
[58] Field of Search ........... 128/341, 270, 271, 260, 128/261, 267; 424/22; 119/14.19, 14.21

[56] References Cited
UNITED STATES PATENTS

| | | | |
|---|---|---|---|
| 1,899,492 | 2/1933 | Beebe | 128/341 |
| 2,368,576 | 1/1945 | Smith | 128/341 |
| 2,832,343 | 4/1958 | Mose | 128/271 |
| 3,690,316 | 9/1972 | Haller | 128/130 |
| 3,703,898 | 11/1972 | Zackheim | 128/261 |

*Primary Examiner*—Aldrich F. Medbery
*Attorney, Agent, or Firm*—James E. Nilles

[57] ABSTRACT

A teat cautery bullet or device for insertion through the teat orifice and into the papillary duct of an injured teat of a dairy cow or similar animal to control hemorrhaging and prevent formation of a blood clot in the teat orifice or papillary duct is formed by molding of solid material which is soluble by liquid in said teat to control such hemorrhaging and clotting. The device comprises a nose portion tapered to facilitate insertion, an integral neck portion tapered to facilitate retention, and an integral base portion to facilitate insertion and removal and of such width as to prevent passage or loss of the device upward into the teat sinus. The soluble material of which the device is molded may consist entirely of one or more soluble active ingredients, such as ferric ammonium sulfate, aluminum ammonium sulfate or aluminum potassium sulfate or may consist of a soluble mixture of one or more of the aforementioned soluble active ingredients and one or more soluble inert binder ingredients, such as amylon, amylum or amylopectin or other starches, which affect the consistency and the solubility of the device. In use, the internally disposed nose and neck portions dissolve before the externally disposed base portion and loss of the device into the teat sinus is prevented.

26 Claims, 3 Drawing Figures

TEAT CAUTERY BULLET

BACKGROUND OF THE INVENTION

1. Field of Use

This invention relates to a pharmaceutical device and composition for use in treating mammals. In particular, it relates to such a device in the form of a teat cautery bullet for insertion in the teat orifice of an injured teat of a dairy cow for purposes of dilation and treatment.

2. Description of the Prior Art

Traumatic injury, or the "stepped on teat", is a common problem in the dairy cow. Infection leading to mastitis and obstruction of the papillary duct which cause hard milking are frequent complications. Further damage to the teat results from leaving milking machines on too long. Blood clots form from the denuded mucosa of the papillary duct, and/or crushed teat sphincter muscle. Incisions, dilation by conical shaped instruments, or curettage of the papillary duct to enlarge the opening also result in hemorrhage and complications of healing.

Various devices and products are already known which are used in the treatment of teat injuries of dairy cows. For example, U.S. Pat. No. 2,832,343 teaches a teat dilator which employs a wooden dilator member or core which is totally nonsoluble and is coated with an active ingredient, such as aspirin, and also a lubricant. Several varieties of medicated teat dilators are on the market which resemble a pipe cleaner stem with a medicated coating over the cloth covering. All of these are essentially a mechanical means of maintaining an open teat with a medicant added to retard infection.

U.S. Pat. No. 2,244,027 teaches a teat dilator which employs a bundle of nonsoluble internal elements made of stiffened flax or the like which is coated with a mixture of active ingredients.

U.S. Pat. No. 2,704,076 discloses a hollow plastic tubular device which serves as a mechanical means for providing an opening into or through the test orifice.

Silver nitrate applicators are used occasionally to control hemorrhage but their effectiveness is quite limited since they are not made in a form that can be retained in the teat sphincter.

SUMMARY OF THE PRESENT INVENTION

In accordance with the present invention there is provided a teat cautery bullet or device for insertion through the teat orifice and into the papillary duct of an injured test of a dairy cow or similar animal to control hemorrhaging and prevent formation of a blood clot in said papillary duct. The device is formed by molding of solid material which is soluble by liquid in said teat to release astringent and styptic ingredients. The device, which is of circular transverse cross-sectional shape and about 21 to 23 millimeters long, comprises a nose portion (about 10 millimeters long) tapered to facilitate insertion, an integral neck portion (about 8 to 10 millimeters long and about 5 millimeters in maximum diameter) tapered to facilitate retention, and an integral base portion (about 3 millimeters long and about 6 millimeters in diameter) to facilitate manual insertion and removal and of such width as to prevent passage or loss of the device upward into the teat sinus. The soluble material of which the device is molded may consist entirely of one or more soluble active ingredients, such as ferric ammonium sulfate, aluminum ammonium sulfate or aluminum potassium sulfate or may consist of a soluble mixture of one or more of the aforementioned soluble active ingredients and one or more soluble inert binder ingredients, such as amylon, amylum or amylopectin or other starches, which affect the consistency and solubility of the device. In a preferred mixture the soluble active ingredient or ingredients comprise about 75% to about 99% of the total weight of the finished device and the soluble inert binder ingredients comprise about 1% to about 25% of the total weight of the finished device. In use, the internally disposed nose and neck portions dissolve before the externally disposed base portion, and loss of the device into the teat sinus is prevented.

DRAWINGS

DESCRIPTION OF A PREFERRED EMBODIMENT

Figure 3:
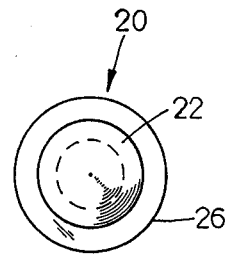
FIG. 3 is an end elevational view taken on line 3—3 of FIG. 2.
Figure 1:
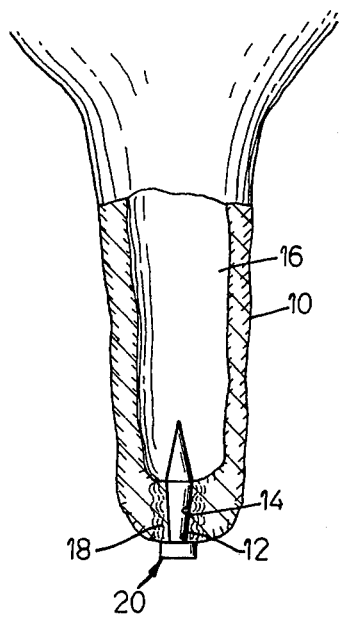
FIG. 1 is an elevational view partly in cross section of the teat of a cow with a cautery bullet or device in accordance with the invention applied thereto.

Referring to FIG. 1, there is shown a cow's teat 10, including a teat orifice 12 at the outer end of a papillary duct 14 which leads to the teat sinus 16. A teat sphincter muscle 18 surrounds the duct 14 and contracts to close the duct.

A teat cautery bullet or device 20 in accordance with the invention is shown inserted through the teat orifice 12 and the papillary duct 14 and extending into the teat sinus 16 of an injured teat of a dairy cow or similar animal and is retained in place by the action of sphincter muscle 18. The device 20 is formed by molding of solid material which is soluble by liquid in said teat to release an astringent and styptic solution to control hemorrhaging and prevent formation of a blood clot in the papillary duct 14. This permits a free stream of milk during the milking operation and allows the papillary duct 14 to heal with a more normal restoration of shape and function.

Figure 2:
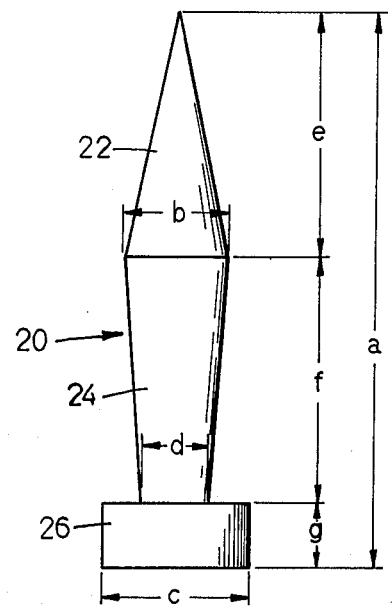
FIG. 2 is an enlarged elevational view of the cautery bullet or device of FIG. 1.

As FIG. 2 shows, the device 20, which is of circular transverse cross section, has a tapered nose portion 22 to facilitate insertion into the teat orifice 12 and through duct 14, a tapered neck portion 24 (integral with portion 22) to enable self-retention in the teat papillary duct 14, and a base portion 26 (integral with portion 24) of greater diameter than the widest portion of the nose portion 22 or neck portion 24 to facilitate gripping with the fingers for manual insertion and removal and to prevent loss of the bullet up into the teat sinus 16. Preferably, device 20 has an overall length (dimension $a$) of about 21 to 23 millimeters, with the nose portion length (dimension $c$) being on the order of 10 millimeters and the nose portion diameter (dimension $b$) being on the order of 5 millimeters. The neck portion length (dimension $f$) is on the order of from 8 to 10 millimeters, whereas the maximum diameter of the neck portion (dimension $b$) is on the order of 5 millimeters and the minimum diameter of the neck portion (dimension $d$) is on the order of from 2 to 3 millimeters. The base portion diameter (dimension $c$) is on the order of 6 millimeters and base portion length or thickness (dimension $g$) is on the order of 3 millimeters. Variations in the length and diameter of the neck portion 24 can be made to accommodate anatomical variations in the size of papillary duct 14. The length of the neck portion (dimension *d*) is designed to fit the length of the papillary duct 14 of the cow. In practice, no individual animals were found which exceeded 10 millimeters length in this dimension.

The soluble material of which the device 20 is molded may consist entirely of one or more soluble active ingredients, such as ferric ammonium sulfate, aluminum ammonium sulfate or aluminum potassium sulfate (each of which has astringent and styptic properties) or may consist of a soluble mixture of one or more of the aforementioned soluble active ingredients and one or more soluble inert binder ingredients, such as amylon, amylum or amylopectin or other starches, which affect the consistency and solubility of the device. In a preferred mixture the soluble active ingredient or ingredients comprise about 75% to about 99% of the total weight of the finished device and the soluble inert binder ingredients comprise about 1% to about 25% of the total weight of the finished device 20.

Official alum is listed as the alum salts of ammonium and potassium. However, Blakiston's NEW GOULD MEDICAL DICTIONARY also lists ammonioferric alum, also called ferric ammonium sulfate, as an astringent and styptic. The official alum (alumen), which may be ammonium alum, $AlNH_4(SO_4)_2.12H_2$), or potassium alum, $AlK(SO_4)_2.12H_2O$, both occur as colorless, odorless crystals or as powder, soluble in water, insoluble in alcohol, and are astringent. Each molecule of the alum crystal has 12 molecules of water bound to it. The ferric ammonium sulfate, $FeNH_4(SO_4)_2.12H_2O$, is astringent and styptic and is also known as ammonioferric alum, ferric alum or iron alum.

Regarding medicinal properties, the action of alum is as a protein precipitate, coagulant of fluids, and constrictor of tissues. In addition to being hemostatic, the coagulant effect is harmful to bacterial cells or other proteinaceous micro-organisms and hence has antiseptic qualities. Alum has been in use for a long time as a pickle ingredient in the preservation of meats and vegetables, presumably for its antibacterial properties. This is not its primary purpose in the application of the teat cautery bullet although it could be beneficial in the event aseptic procedure was broken. The astringent and styptic properties of the active ingredients produce the desired hemostatic effect.

Blakiston's medical dictionary lists both amylon and amylum as starch. The difference may be whether it is derived from wheat or corn, but the distinction is not clear. It is commonly marketed as cornstarch in this country.

In use, the internally disposed nose and neck portions 22 and 24, respectively, dissolve before the externally disposed base portion 26 and loss of the device 20 into the teat sinus is prevented.

The aluminum ammonium sulfate and aluminum potassium sulfate are forms of alum which may be melted and poured into a mold in a manner similar to the casting of many metal products to form device 20. After cooling, the material solidifies and retains its shape well. The inert ingredient is intended principally to dilute the active ingredient (thereby controlling solubility and dosage) and also to affect the hardness or consistency of the device 20.

The cornstrach was melted and blended with alum at temperatures ranging from 250° to 300°F. There is molecular water contained in the alum compound, and it will change to the liquid state upon heating without the addition of water. Starch is insoluble in cold water. Therefore, it would appear that heat is necessary to dissolve starch in alum in this application, although it is possible that one might arrive at another method of combining the two substances.

In actual tests up to 25% starch was combined or mixed in the hot liquid alum, with and without the addition of water (one to several drops), and no incompatibility between the two substances could be detected. The only detectable difference was in the final hardness and solubility of the bullet after it had cooled and solidified.

More specifically, the base portion 26 which is outside and exposed to air will dissolve at a slower rate than portions 22 and 24, or not at all, and if the device 20 is forgotten or left in place accidentally, it will simply fall out when a sufficient amount of the upper end has dissolved.

Dissolution of the bullet 20 will occur in one to four hours depending on (1) the diameter of the neck of the bullet, (2) how much the papillary duct is enlarged during the procedure, and (3) whether or not leakage of milk occurs around the bullet when it is in place in the duct.

The teat cautery bullet or device 20 is employed in practice as follows:

1. The affected quarter 10 should not be completely milked out prior to being operated upon. This provides for flushing of the teat sinus 16 and associated papillary duct 14 during the operation, and allows the operator to make a better judgment of the size of the existing opening 12 and what surgical procedure will best restore the desired size opening. It is important that a free stream of milk be obtained by hand milking pressure without excessive force.
2. Restraint of the animal can be by the method preferred by the operator. Conventional restraint by halter or nose lead on the head, and lifting of one hind leg by lariat rope with one end of the rope tied in a bowline knot just above the hock and the other end of the rope over an overhead beam is satisfactory.

Local injection of anesthetic may be indicated in some cases; however, it should be born in mind that such injections into the area of the teat sphincter will cause some distortion of the tissue and make judgment of the size of the teat orifice more difficult.

3. Aseptic technique with sterilized instruments is necessary.
4. Thoroughly cleanse teat 10 with detergent and water, dry, and apply merthiolate or other suitable antiseptic. Hand milk several streams of milk from the teat 10 to flush away residual disease organisms in the teat sinus 16 and papillary duct 14.
5. If the teat orifice 12 is closed completely, it may be first opened with a sharp intravenous needle, or scalpel equipped with, for example, number 11 Bard-Parker blade. A partially obstructed duct 14 can be stretched slightly with a conical test dilator and then enlarged using quick strokes of a teat curette. If the test 10 has been split, sutures may be required to approximate the cut surfaces and retain the teat cautery bullet 20.

The teat 10 should be opened to the point that a free stream of milk is obtained by normal hand milking pressure. If the quarter has not been milked out, leaking may occur. Contraction of the tissues during healing will stop small leakages.

6. Insert the teat cautery bullet 20 into the teat orifice 12 and observe that it remains in place in the papillary duct 14. It may be left in place until the next milking period. A severely damaged teat 10 may still leak milk around the bullet 20. This can be tolerated so long as the bullet 20 remains in place until hemostasis has been achieved.

7. Completely cover the end of the teat 10 with an antiseptic cream or ointment, such as merthiolate cream. The ointment should have enough viscosity to keep contaminants out of the wound.

One treatment is sufficient unless re-injury occurs. Re-injury and additional hemorrhage can of course occur, from the vacuum and pulsating effect of a milking machine on a badly lacerated teat. If discomfort is evidenced by the cow when the milking machine is applied, an alternate method of removing milk from the affected quarter is by the use of a sterilized milk tube or teat infusion cannula.

The procedure for aftercare is as follows:

The entire teat 10 should be thoroughly cleansed before milking to remove contaminants which may enter the teat during the milking operation. Continue use of antiseptic cream on the end of the teat immediately after milking until final healing has occurred. Parenteral and local antibiotic use is often indicated during the treatment of teat injuries. Milk should not be sold for human consumption until the withdrawal period has been observed.

I claim:

1. A teat cautery bullet shaped device for insertion through a teat orifice and into the papillary duct of an injured teat of a dairy cow or similar animal to control hemorrhaging and prevent formation of blood clots in the papillary duct, said device being formed of solid material having astringent and styptic qualities which is soluble by liquid in said teat to control such hemorrhaging and clotting, said device comprising a nose portion shaped to facilitate insertion, an integral neck portion shaped to facilitate retention by the teat sphincter muscles surrounding said papillary duct, and an integral base portion shaped to facilitate manual insertion and removal and to prevent passage or loss of the device upward into the teat sinus.

2. A device according to claim 1 wherein said material consists entirely of at least one soluble active ingredient.

3. A device according to claim 2 wherein said one soluble active ingredient is selected from a class of ingredients consisting of ferric ammonium sulfate, aluminum ammonium sulfate and aluminum potassium sulfate.

4. A device according to claim 1 wherein said material consists entirely of a plurality of soluble active ingredients.

5. A device according to claim 4 wherein each of said soluble active ingredients is selected from a class of ingredients consisting of ferric ammonium sulfate, aluminum ammonium sulfate and aluminum potassium sulfate.

6. A device according to claim 1 wherein said soluble material comprises a soluble mixture of at least one soluble active ingredient and at least one soluble binder ingredient.

7. A device according to claim 6 wherein said binder ingredient is starch.

8. A device according to claim 7 wherein said starch is selected from a class consisting of amylon and amylopectin.

9. A device according to claim 6 wherein said one soluble active ingredient is selected from a class of ingredients consisting of ferric ammonium sulfate, aluminum ammonium sulfate and aluminum potassium sulfate.

10. A device according to claim 9 wherein said binder ingredient is starch.

11. A device according to claim 10 wherein said starch is selected from a class consisting of amylon and amylopectin.

12. A device according to claim 6 wherein said mixture comprises about 75% to about 99% by weight of said active ingredient and the remainder by weight being said binder ingredient.

13. A device according to claim 1 which is of generally circular transverse cross section and wherein said nose portion is tapered and said neck portion is tapered.

14. A teat cautery bullet or device of generally circular transverse cross section for insertion through a teat orifice and into the papillary duct of an injured teat of a dairy cow or similar animal to control hemorrhaging and prevent formation of blood clots in said papillary duct, said device being formed of solid material having astringent and styptic qualities which is soluble by liquid in said teat to control such hemorrhaging and clotting, said device comprising a nose portion tapered to facilitate insertion, an integral neck portion at least as long as said papillary duct and tapered to facilitate retention by the teat sphincter muscles surrounding said papillary duct, and an integral base portion shaped to facilitate manual insertion and removal and wider than said nose portion and said neck portions to prevent passage or loss of the device upward into the teat sinus.

15. A device according to claim 14 wherein said material consists entirely of at least one soluble active ingredient.

16. A device according to claim 15 wherein said one soluble active ingredient is selected from a class of ingredients consisting of ferric ammonium sulfate, aluminum ammonium sulfate and aluminum potassium sulfate.

17. A device according to claim 14 wherein said material consists entirely of a plurality of soluble active ingredients.

18. A device according to claim 17 wherein each of said soluble active ingredients is selected from a class of ingredients consisting of ferric ammonium sulfate, aluminum ammonium sulfate and aluminum potassium sulfate.

19. A device according to claim 14 wherein said soluble material comprises a soluble mixture of at least one soluble active ingredient comprising about 75% to about 99% of the total weight of said device and at least one soluble binder ingredient comprising the remainder of the total weight of said device.

20. A device according to claim 19 wherein said binder ingredient is starch.

21. A device according to claim 20 wherein said starch is selected from a class consisting of amylon and amylopectin.

22. A device according to claim 19 wherein said one soluble active ingredient is selected from a class of ingredients consisting of ferric ammonium sulfate, aluminum ammonium sulfate and aluminum potassium sulfate.

23. A device according to claim 22 wherein said binder ingredient is starch.

24. A device according to claim 23 wherein said starch is selected from a class consisting of amylon and amylopectin.

25. A device according to claim 14 wherein said neck portion is about 8 to 10 millimeters in length, wherein said neck portion tapers from a maximum diameter of about 5 millimeters to a minimum diameter of about 2 to 3 millimeters, and wherein said base portion is about 6 millimeters in diameter.

26. A device according to claim 25 wherein said nose portion is about 10 millimeters in length and wherein said base portion is about 3 millimeters in length.

* * * * *